(12) United States Patent
Heger et al.

(10) Patent No.: US 7,687,071 B1
(45) Date of Patent: Mar. 30, 2010

(54) NANOPARTICULATE CORE SHELL SYSTEMS AND THE USE THEREOF IN PHARMACEUTICAL AND COSMETIC PREPARATION

(75) Inventors: Robert Heger, Heidelberg (DE); Helmut Auweter, Limburgerhof (DE); Jörg Breitenbach, Mannheim (DE); Heribert Bohn, Wattenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 695 days.

(21) Appl. No.: 09/857,480

(22) PCT Filed: Dec. 7, 1999

(86) PCT No.: PCT/EP99/09545

§ 371 (c)(1),
(2), (4) Date: Aug. 13, 2002

(87) PCT Pub. No.: WO00/33820

PCT Pub. Date: Jun. 15, 2000

(30) Foreign Application Priority Data

Dec. 8, 1998 (DE) ................ 198 56 432

(51) Int. Cl.
*A61K 9/14* (2006.01)
(52) U.S. Cl. .............. 424/489; 424/490; 424/491; 424/492; 424/493; 424/496; 424/497; 424/501
(58) Field of Classification Search ........ 424/486, 424/489, 495, 499, 485, 487, 490–497, 423, 424/451, 464, 465, 429
See application file for complete search history.

(56) References Cited

U.S. PATENT DOCUMENTS

| | | | |
|---|---|---|---|
| 4,826,689 A | | 5/1989 | Violanto |
| 4,935,245 A | | 6/1990 | Horn |
| 5,118,528 A | | 6/1992 | Fessi |
| 5,133,908 A | * | 7/1992 | Stainmesse et al. ......... 264/4.1 |
| 5,145,684 A | * | 9/1992 | Liversidge et al. .......... 424/489 |
| 5,389,382 A | * | 2/1995 | List et al. ................... 424/499 |
| 5,399,363 A | | 3/1995 | Liversidge |
| 5,858,410 A | | 1/1999 | Mueller |
| 6,045,829 A | * | 4/2000 | Liversidge et al. .......... 424/489 |
| 6,068,857 A | * | 5/2000 | Weitschies et al. ......... 424/489 |
| 6,190,692 B1 | * | 2/2001 | Busetti et al. .............. 424/451 |
| 6,761,908 B1 | * | 7/2004 | Roreger ..................... 424/484 |

FOREIGN PATENT DOCUMENTS

| | | |
|---|---|---|
| CA | 2028665 | 4/1991 |
| DE | 37 42 473 | 7/1988 |
| DE | 44 40 337 | 5/1996 |
| EP | 169 618 | 1/1986 |
| EP | 275 796 | 7/1988 |
| EP | 276 735 | 8/1988 |
| EP | 425 892 | 5/1991 |
| EP | 605 497 | 7/1994 |
| EP | 0 717 989 A1 * | 6/1996 |
| WO | 93/25221 | 12/1993 |
| WO | 95/05164 | 2/1995 |
| WO | 97/14407 | 4/1997 |
| WO | 98/14174 | 4/1998 |

* cited by examiner

*Primary Examiner*—Michael G Hartley
*Assistant Examiner*—Micah-Paul Young
(74) *Attorney, Agent, or Firm*—Novak Druce + Quigg LLP (57) ABSTRACT

Nanoparticulate preparations of pharmaceutical and cosmetic active substances with a core-shell structure, whereby the active substance is present in an X-ray amorphous form, together with a polymer matrix and the shell consists of a stabilizing sheathing matrix.

12 Claims, 1 Drawing Sheet

Fig. 1

NANOPARTICULATE CORE SHELL SYSTEMS AND THE USE THEREOF IN PHARMACEUTICAL AND COSMETIC PREPARATION

The present invention relates to nanoparticulate preparations of pharmaceutical active ingredients with a core/shell structure, where the active ingredient is present in the core in X-ray amorphous form together with at least one polymer, and the shell consists of a polymeric coating matrix.

EP-A 425 892 discloses a method for improving the bioavailability of pharmaceutical active ingredients with peptide linkages, wherein a solution of the active ingredient in a water-miscible organic solvent is rapidly mixed with an aqueous colloid so that the active ingredient precipitates in colloidal form.

EP-A 276 735 describes active ingredient particles which are enveloped in a protective colloid and in which the active ingredient is dispersed in an oil phase. However, problems of compatibility frequently arise in oil phases.

EP-A-0169 discloses particulate pharmaceutical preparations of substances of low solubility in water, where the preparations are obtained by precipitating from a solution of the active ingredient after addition of a precipitating solution.

WO 93/10767 describes oral administration forms for peptide drugs in which the drug is incorporated in a gelatin matrix in such a way that the colloidal particles which form have a neutral charge. However, the disadvantage of such forms is their tendency to flocculate.

EP-A 0605 497 describes nanoparticles in which the active ingredient is stabilized in a lipid matrix. However, lipid matrices are unstable to shear forces, which may cause problems in further processing.

DE-A 4440337 describes the preparation of nanosuspensions stabilized with surfactants. However, in some circumstances, high surfactant concentrations are physiologically unacceptable.

U.S. Pat. No. 5,145,684 and U.S. Pat. No. 5,399,363 describe the preparation of crystalline nanoparticles by special grinding processes. However, the bioavailability from crystalline nanoparticles is generally relatively poor and they may, moreover, cause problems because of the polymorphism of some active ingredients.

U.S. Pat. No. 4,826,689 describes a precipitation process in which amorphous spherical particles stabilized by no further addition or only small additions of surfactants are obtained. The shear stability of such systems and the possibility of sterilization are small.

EP-A 275,796 describes the preparation of colloidal dispersible systems with spherical particles below 500 nm in size and having a matrix structure, not a core/shell structure.

WO 97/14407 describes the preparation of nanoparticles by expansion from a solvent in a compressed gas, liquid or a supercritical fluid in the presence of an amphiphile.

DE 3742 473 C2 describes hydrosols of solid particles of a ciclosporin and a stabilizer which maintains the degree of dispersion of the particles. The particle size is in the colloidal range in these hydrosols. It is pointed out in particular that the described hydrosol particles consist of active ingredient mass.

However, a disadvantage of these hydrosols is that the size of the hydrosol particles increases greatly over the course of time. This is particularly true when the dispersing phase of the hydrosol contains active ingredient solvent. It is obligatory to employ this active ingredient solvent when preparing the hydrosol particles and it must then be removed as quickly as possible.

The growth of hydrosol particles is attributable to what is called Ostwald ripening in which active ingredient molecules are transported via the dispersing phase from small hydrosol particles to large hydrosol particles. This means that smaller particles slowly dissolve and larger particles slowly grow. Since the active ingredient ciclosporin has a slight residual solubility even in solvent-free water, it is not possible to prevent the hydrosol particles growing even in that case.

Concerning the stability of the nanoparticulate systems, the presence of the active ingredient in stable amorphous form and the wide applicability in a large number of pharmaceutical dosage forms, however, there was still room for improvement.

It is an object of the present invention to find improved active ingredient-containing nanoparticulate preparations.

We have found that this object is achieved by the nanoparticulate preparations of pharmaceutical active ingredients which have a core/shell structure, where the active ingredient is present in the core in X-ray amorphous form in a polymer matrix, and the shell consists of a stabilizing coating matrix of a polymer with protective colloid properties.

There are preferably at least two separate phases in the core, with one phase consisting of discrete, X-ray amorphous particles of the active ingredient, while the other phase is a molecular dispersion of the active ingredient in one or more polymers. The ratio of the amounts of core polymers to active ingredient essentially determines whether the core is one phase or two phases.

The decisive factor is that as the size of the active ingredient particles decreases the pressure on the substance to dissolve increases. This results in an increased saturation solubility. The increased saturation solubility leads, according to Noyes-Whitney, to an increase in the rate of dissolution. An additional factor is that the bioactive substance is present in the formulations according to the invention in an energetically unstable, metastable state. If the nanoparticle is insufficiently stabilized, this may lead in some cases to spontaneous crystallization, and the active ingredient precipitates out of the stabilized form.

The search was therefore also for solutions apart from a stable shell structure which also withstands procedures such as mixing into creams or ointments, homogenization in cosmetic preparations and the pressure and shear stresses during sterilization.

Surprisingly, the colloidal active ingredient preparations according to the invention show distinctly less growth of hydrosol particles than known active ingredient preparations which consist essentially exclusively of active ingredient mass in the core of the colloidal particles. One hour after the aqueous hydrosols have been prepared in the presence of a solvent dissolving the active ingredient, the particle growth is a factor of 4 to 10 less. In the case of aqueous hydrosols which contain no solvent dissolving the active ingredient, the particle growth is reduced by a factor of 1.5-5.

The colloidal particles present in the active ingredient preparation according to the invention have a polymer coating which envelops the core of the particles. The task of this polymer coating is to stabilize the particles in their colloidal state so as to prevent heterogeneous particle growth (aggregation, flocculation etc.).

In addition, the colloidal particles present in the active ingredient preparation according to the invention have a core of active ingredient and polymer. The active ingredient in the interior of this core is present in X-ray amorphous form. It is essential that no crystalline active ingredient fractions are detectable (X-ray diffraction) in the active ingredient preparation. In particular, the polymers in the interior of the particles contribute to maintaining the active ingredient in its noncrystalline state and to stabilizing the colloidal structures in relation to homogeneous particle growth (Ostwald ripening).

Suitable polymeric stabilizers for the coating matrix of the shell according to the invention are swellable protective colloids such as, for example, bovine, porcine or fish gelatin, starch, dextrin, pectin, gum arabic, ligninsulfonates, chitosan, polystyrenesulfonate, alginates, casein, caseinate, methylcellulose, carboxymethylcellulose, hydroxypropylcellulose, milk powder, dextran, whole milk or skim milk or mixtures of these protective colloids. Also suitable are homo- and copolymers based on the following monomers: ethylene oxide, propylene oxide, acrylic acid, maleic anhydride, lactic acid, N-vinylpyrrolidone, vinyl acetate, $\alpha$- and $\beta$-aspartic acid. It is particularly preferred to use one of the gelatin types mentioned, in particular gelatin degraded with acid or base and having Bloom numbers in the range from 0 to 250, very particularly preferably gelatin A 100, A 200, B 100 and B 200, and low molecular weight, enzymatically degraded gelatin types with a Bloom number of 0 and molecular weights of from 15,000 to 25,000 D, such as, for example, Collagel A and Gelitasol P (supplied by Stoess, Eberbach) and mixtures of these gelatin types.

The preparations additionally contain low molecular weights of surface-active compounds. Particularly suitable as such are amphiphilic compounds or mixtures of such compounds. Suitable in principle are all surfactants with an HLB of from 5 to 20. Examples of suitable surface-active substances are: esters of long-chain fatty acids with ascorbic acid, mono- and diglycerides of fatty acids and their ethoxylation products, esters of mono-fatty acid glycerides with acetic acid, citric acid, lactic acid or diacetyltartaric acid, polyglycerol fatty acid esters such as, for example, the monostearate of triglycerol, sorbitan fatty acid esters, propylene glycol fatty acid esters, 2-(2-stearoyllactyl)lactic acid salts and lecithin. Ascorbyl palmitate is particularly preferably employed.

Suitable polymeric constituents present in the core of the particles of the active ingredient preparation according to the invention are in principle all polymers which are insoluble or only partly soluble in water or aqueous solutions or water/solvent mixtures in a temperature range between 0 and 240° C., a pressure range between 1 and 100 bar, a pH range from 0 to 14 or ionic strengths up to 10 mol/l.

Insoluble or only partly soluble means in this connection that the second virial coefficient for the polymer(s) in water or a mixture of water and an organic solvent can assume values of less than zero (cf. M. D. Lechner, "Makromolekulare Chemie", Birkhäuser Verlag, Basle, pp. 170-175). The second virial coefficient, which provides information on the behavior of a polymer in a solvent (mixture), can be determined experimentally, for example by light scattering measurement or determination of the osmotic pressure. The units of this coefficient are $(mol\text{-}l)/g^2$.

It is possible to employ one or more polymers. The molecular weights of the polymers used are in the range 1000-10,000,000 g/mol, preferably in the range 1000-1,000,000 g/mol. All polymers suitable for use in drugs and cosmetics are suitable in principle.

Polymers of particular interest are those which are soluble in water-miscible organic solvents, and insoluble or only partly soluble in water or aqueous solutions or water/solvent mixtures at temperatures between 0 and 240° C. The following polymers are mentioned by way of example but without being limiting:

Poly(vinyl ethers) such as, for example, poly(benzyloxyethylene), poly(vinyl acetals), poly(vinyl ketones), poly(allyl alcohol), poly(vinyl esters) such as, for example, poly(vinyl acetate), poly(oxytetramethylene), poly(glutaraldehyde), poly(carbonates), poly(esters), poly(siloxanes), D,L-poly(lactide), poly(lactide), poly(glycolide), poly(D,L-lactide-co-glycolide), poly(amides), poly(piperazines), poly(anhydrides) such as, for example, poly(methacrylic anhydride), gutta percha, cellulose ethers such as, for example, methylcellulose (degree of substitution 3-10%), ethylcellulose, butylcellulose, cellulose esters such as, for example, cellulose acetate or starches. In particular copolymers and block copolymers of the monomers of the above-mentioned polymers. In addition copolymers and block copolymers of polyesters and hydroxy carboxylic acids and linear and star polyethylene glycol, for example AB and ABA block copolymers of D,L-poly(lactide) and polyethylene glycol or poly(glycolide).

Also of particular interest are polymers which have an upper and/or lower miscibility limit at temperatures between 0 and 240° C. in water or aqueous solutions or water/solvent mixtures, i.e. these polymers can be precipitated from corresponding solutions by raising or lowering the temperature. The following polymers are mentioned by way of example but without being limiting:

Poly(acrylamides), poly(methacrylamides) such as, for example, poly(N-isopropylacrylamide), poly(N,N-dimethylacrylamide), poly(N-(1,1-dimethyl-3-oxobutyl)acrylamide), poly(methoxyethylene), poly(vinyl alcohols), acetylated poly(vinyl alcohols), poly(oxyethylene), cellulose ethers such as, for example, methylcellulose (degree of substitution 20-40%), isopropylcellulose, cellulose esters, starches, modified starches such as, for example, methylether starch, gum arabic, and copolymers or block copolymers from monomers of the above-mentioned compounds. In particular AB or ABA block copolymers based on ethylene oxide and propylene oxide, e.g. poloxamers such as poloxamer 188 and poloxamer 407.

Also of particular interest are polymers which can be precipitated from corresponding solutions by altering the pH or the ionic strength at temperatures between 0 and 240° C. in water or aqueous solutions or water/solvent mixtures. The following polymers are mentioned by way of example but without being limiting:

alginates, chitosan, chitin, shellac, polyelectrolytes, poly(acrylic acid), poly(methacrylic acid), poly(methacrylic esters) with secondary, tertiary or quaternary amino groups, in particular copolymers or block copolymers based on various acrylates, methacrylates, methacrylic acid, acrylic acid, e.g. a copolymer of methacrylic acid/methacrylic ester (MA/MAE ratio by weight 1:1 or 1:2) or a copolymer of dimethylaminoethyl methacrylate and methacrylic ester in the ratio 1:1 by weight (Eudragit® types).

The amounts of the various components are chosen according to the invention so that the preparations contain 0.1 to 70% by weight, preferably 1 to 40% by weight, of active ingredient, 1 to 80% by weight, preferably 10 to 60% by weight, of one or more polymeric stabilizers (coating polymer), 0.01 to 50% by weight, preferably 0.1 to 30% by weight, of one or more polymers for the core, and 0 to 50% by weight, preferably 0.5 to 10% by weight, of one or more low molecular weight stabilizers. The percent by weight data are based on a dry powder.

In addition, the preparations may also contain antioxidants and/or preservatives to protect the active ingredient. Examples of suitable antioxidants or preservatives are α-tocopherol, t-butylhydroxytoluene, t-butylhydroxyanisole, lecithin, ethoxyquin, methylparaben, propylparaben, sorbic acid, sodium benzoate or ascorbyl palmitate. The antioxidants or preservatives may be present in amounts of from 0 to 10% of the total weight of the preparation.

The preparations may also contain plasticizers to increase stability of the final product. Examples of suitable plasticizers are sugars and sugar alcohols such as sucrose, glucose, lactose, invert sugar, sorbitol, mannitol, xylitol or glycerol. Lactose is preferably employed as plasticizer. The plasticizers can be present in amounts of from 0 to 50% by weight.

Further pharmaceutical aids such as binders, disintegrants, flavorings, vitamins, colors, wetting agents, additions to influence the pH (cf. H. Sucker et al., Pharmazeutische Technologie, Thieme-Verlag, Stuttgart 1978) can likewise be introduced via the organic solvent or the aqueous phase.

To carry out the process according to the invention, firstly a solution of the active ingredient is prepared in a suitable solvent, with solution meaning in this connection a true molecularly disperse solution or a melt emulsion. Depending on the active ingredient, it is possible to employ temperatures of 0-250° C. and pressures of up to 100 bar for this. Suitable solvents are organic, water-miscible solvents which are volatile and thermally stable and contain only carbon, hydrogen, oxygen, nitrogen and sulfur. They are expediently at least 10% by weight miscible with water and have a boiling point below 200° C. and/or have fewer than 10 carbon atoms. Appropriate alcohols, esters, ketones, ethers and acetals are preferred. Those particularly used are ethanol, n-propanol, isopropanol, butyl acetate, ethyl acetate, tetrahydrofuran, acetone, 1,2-propanediol 1-n-propyl ether or 1,2-butanediol 1-methyl ether. Ethanol, isopropanol and acetone are very particularly preferred.

In one embodiment of the process, a molecularly disperse solution of the active ingredient in the chosen solvent is prepared together with the polymer which is to be present in the active ingredient preparation in the core of the particles. This polymer has the property of being insoluble or only partly soluble in water in a particular temperature, pH or salt range.

The concentration of the active ingredient/polymer solution prepared in this way is generally from 10 to 500 g of active ingredient per 1 kg of solvent and 0.01 to 400 g of polymer, with the polymer/active ingredient ratio by weight being between 0.01 to 1 and 5 to 1. In a preferred embodiment of the process, the low molecular weight stabilizer is added directly to the active ingredient/polymer solution.

In a process step following this, the active ingredient/polymer solution is mixed with an aqueous solution of the polymeric coating material. The concentration of the polymeric coating material is from 0.1 to 200 g/l, preferably 1 to 100 g/l.

In a further embodiment of the process, a molecularly disperse solution of the active ingredient in the chosen solvent is prepared without the polymer which is to be present in the active ingredient preparation in the core of the particles. The concentration of the active ingredient solution prepared in this way is generally from 10 to 500 g of active ingredient per 1 kg of solvent.

In a subsequent process step, this solution is mixed with an aqueous molecular solution of the polymer which is to be present in the active ingredient preparation in the core of the particles. The concentration of the polymer solution prepared in this way is generally from 0.01 to 400 g of polymer. The temperatures, pH values and salt concentrations of the two solutions which are to be combined are chosen so that the active ingredient and the polymer are insoluble after the solutions have been combined. In a preferred embodiment of the process, the low molecular weight stabilizer is added directly to the active ingredient solution.

In a process step following this, the active ingredient/polymer precipitate is mixed with an aqueous solution of the polymeric coating material. The concentration of the polymeric coating material is from 0.1 to 200 g/l, preferably 1 to 100 g/l.

In order to minimize the size of the particles obtained in the mixing process, it is advisable for the mechanical energy input during mixing of the ciclosporin solution with the solution of the coating material to be high. Such an energy input is possible, for example, by vigorous stirring or shaking in a suitable apparatus, or by spraying the two components in a compact jet into a mixing chamber so that vigorous mixing takes place.

The mixing process can be carried out batchwise or, preferably, continuously. The mixing process results in precipitation. The resulting suspension or colloid can then be converted in a manner known per se into a dry powder, for example by spray drying, freeze drying or fluidized bed drying.

The conditions to be chosen in the specific case in relation to varying the water/organic solvent system, the pH values, the temperatures or the ionic strengths when carrying out the process according to the invention can be established by the skilled worker by a few simple preliminary tests on the appropriate polymer with the aid of the second virial coefficient.

The initial dispersion can then be subjected to drying processes known to the skilled worker.

Accordingly, the nanoparticulate systems according to the invention can, after the preparation, also be dried, for example by spray drying or lyophilization, and then redispersed again with virtually the same particle size distribution. This is a great advantage for all applications in which the preparation must be stored for as long as possible, is exposed to extreme stresses such as heat or cold, or is to be transferred from an aqueous carrier into other carriers as solvents. This means that the preparations according to the invention are no longer bound to the solvent with which they were prepared.

On lyophilization of the nanoparticles according to the invention, it is possible to add cryoprotective substances such as, for example, trehalose or polyvinylpyrrolidones.

It is thus possible to obtain according to the invention dry powders which do not lose the properties they acquired in the initial dispersion. This means that the amorphous nature of the active ingredient and core/shell structure are retained. It is a further property according to the invention that, on redissolving, these dispersions have the same particle size distribution, with a variation of 20%, preferably <15%, which they had as initial dispersion.

The interfacial tension of the nanoparticulate dispersions according to the invention is 20-40 mN/m, preferably 10-30 nM/m.

The particle sizes of the core/shell structures are in the range from 0.01 to 2 μm, preferably 0.05 to 0.9 μm.

Active ingredients of low solubility according to the invention particularly preferably have a solubility of less than 10 mg/ml of water at 25° C.

Examples of suitable active ingredients are:

analgesics/antirheumatics such as codeine, diclofenac, fentanyl, hydromorphone, ibuprofen, indomethacin, levomethadone, morphine, naproxen, piritramide, piroxicam, tramadol antiallergics such as astemizole, dimetindene, doxylamine, loratadine, meclozine, pheniramine, terfenadine antibiotics/chemotherapeutics such as erythromycin, framycetin, fusidic acid, rifampicine, tetracycline, thiacetazone, tyrothricin antiepileptics such as carbamazepine, clonazepam, mesuximide, phenyloin, valproic acid antimycotics such as clotrimazole, fluconazole, itraconazole calcium channel blockers such as darodipine, isradipine corticoids such as aldosterone, betametasone, budesonide, dexametasone, fluocortolone, fludrocortisone, hydroxycortisone, methylprednisolone, prednisolone hypnotics/sedatives benzodiazepines, cyclobarbital, methaqualone, phenobarbital immunosuppressants azathioprine, ciclosporin local anesthetics benzocaine, butanilacaine, etidocaine, lidocaine, oxybuprocaine, tetracaine migraine remedies dihydroergotamine, ergotamine, lisuride, methysergide anesthetics droperidol, etomidate, fentanyl, ketamine, methohexital, propofol, thiopental opthalmologicals acetazolamide, betaxolol, bupranolol, carbachol, carteolol, cyclodrine, cyclopentolate, diclofenamide, edoxudine, homatropine, levobunolol, pholedrine, pindolol, timolol, tropicamide phytopharmaceuticals

*hypericum, urtica* folia, artichoke, *Agnus castus, cimicifuga*, devil's claw, broom, peppermint oil, eucalyptus, celandine, ivy, kava-kava, *echinacea*, valerian, palmetto extract, milk thistle, *Ginkgo biloba, Aloe barbadensis, Allium sativum, Panax ginseng, Serenoa repens, Hydrastis canadensis, Vaccinium macrocarpon* or mixtures thereof protease inhibitors e.g. saquinavir, indinavir, ritonavir, nelfinavir, palinavir or combinations of these protease inhibitors sex hormones and their antagonists anabolics, androgens, antiandrogens, estradiols, gestagens, progesterone, estrogens, antiestrogens such as tamoxifen vitamins/antioxidants such as carotenoids or carotenoid analogs, for example β-carotene, canthaxanthin, astaxanthin, lycopene or lipoic acid cytostatics/antimetastatics busulfan, carmustine, chlorambucil, cyclophosphamide, dacarbazine, dactinomycin, estramustine, etoposide, fluorouracil, ifosfamide, methotrexate, paclitaxel, vinblastine, vincristine, vindesine.

The nanoparticulate preparations according to the invention are suitable in principle for producing all pharmaceutical dosage forms: oral drug forms, topical drug forms such as dermatologicals, ophthalmalogicals, pulmonary or nasal forms, buccal forms, anal or intravaginal forms, enteral and parenteral forms.

It is thus possible to process the preparations according to the invention to tablets, pellets, sachets, drinkable formulations, suppositories, injection solutions or capsule fillings.

Thus, for example, formulation in soft or hard gelatin preparations is possible. Formulations of these types then represent examples of multiparticulate systems in which the nanoparticles which is one phase the preparation of the soft gelatin matrix is another phase which, moreover, may contain another or the same active ingredient.

In the same way, the systems according to the invention can also be introduced into other matrices and, in this case, represent a separate phase from the remaining matrix. Matrices of this type may be tablets, suppositories or systems for pulmonary administration or transdermal administration.

In connection with amorphous active ingredient embedding, mention must also be made of a particular property of active ingredients, polymorphism. Many active ingredients exist in more than one crystalline form. It can generally be assumed that more than 50% of all active ingredients exist in several crystalline forms. All these polymorphic modifications of an active ingredient are chemically identical but have different physical properties such as melting point, density and solubility. This means that the different modifications also have an effect on the processability and, in the most critical case, also on the bioavailability.

The preparations according to the invention make it possible in a simple manner to convert active ingredients into the amorphous state and can use as starting materials also products of widely varying particle size distribution as well as amorphous bulk materials, and thus avoid the problem of different polymorphic forms and the possible disadvantages associated therewith relating to solubility, storage stability and bioavailability.

It was also an object of the present invention to find novel formulations for the nanoparticulate amorphous core/shell structures. It was surprisingly possible, after adaptation of the polymeric stabilizers employed, to meet the requirements for injectable products, to obtain stable core/shell structures also with gelatin hydrolyzates. The advantage of using such gelatin hydrolyzates is that the histamine response in vivo on administration as intravenous, intramuscular or subcutaneous administration is distinctly less.

The nanoparticles according to the invention make aseptic preparation and sterile filtration possible.

Since solid tumors have the ability to filter particles out of the bloodstream, the preparations according to the invention are suitable for achieving tumor targeting. It is thus possible to achieve locally highly concentrated accumulations of cytotoxic substances. This means that therapy of cancers by the nanoparticulate systems according to the invention is particularly preferred.

Cytostatics suitable and preferred for the technology according to the invention are taxols such as paclitaxel, cisplatin, but also non-intercalating farnesyltransferase inhibitors.

It is further known that nanoparticulate systems are able to overcome the blood-brain barrier and thus can be employed, in particular, in the area of therapy of CNS disorders. The same also applies to the nanoparticles according to the invention, which are thus also suitable in particular for use for treatments of disorders in the area of the CNS.

Although the polymer weight is distinctly lower than in the forms described in EP-A 425 892, it is possible to obtain stable products which are adapted to requirements. The small number of ancillary substances is an advantage compared with other processes. The preparations according to the invention of the amorphous core/shell nanoparticles often consist only of the polymeric carrier and the bioactive substance.

The amorphous core/shell nanoparticles according to the invention have another advantage because of the process. The vigorous mixing of the bioactive substance from a solvent into a non-solvent makes it possible to introduce small amounts of the polymer, which later aggregates by adsorption onto the surface during the formation of the spherical structure, into the matrix. This contributes to stabilizing the amorphous and thus metastable state. It specifically comprises a multiphase system with an outer shell composed of the polymeric addition responsible for the dispersion, and of an amorphous structure which contains, still dissolved, the same polymeric addition or another addition as crystallization inhibitor.

A special situation is the occurrence of liquid crystalline systems in the amorphous phase of the preparations according to the invention.

Preparations of low molecular weight peptides such as, for example, LMWH make administration possible by the oral route and, advantageously, with an identical formulation as injection, the administration route which is at present employed as standard for deep vein thrombosis.

In general, it can be stated that the preparations according to the invention can be employed advantageously in virtually all administration forms based on only a single formulation.

The preparations according to the invention are also suitable for colon targeting.

It is likewise possible according to the invention to obtain injectable depot products.

The preparations according to the invention can also be employed in parenteral alimentation. In this connection the preparation according to the invention can be used in particular for formulating vitamins and amino acids.

In nicotine replacement therapy it is possible with the preparations according to the invention, e.g. with nicotine tartrate or nicotine base, to achieve the necessary plasma peaks which are particularly important in the cessation process.

Topical application for hair growth active ingredients such as minoxidil is also advantageous with the preparation according to the invention. The hair follicles can be reached better because of the structure.

In the pulmonary administration of the preparations according to the invention, apart from the administration of asthma therapeutics such as budesonide and cytostatics, in particular the administration of protein and peptide therapeutics is contemplated. Examples are vasopressin analog, LHRH antagonists, glucagon, parathyroid hormone, calcitonin, insulin, LHRH analog leuprolide, granulocyte colony stimulating factor and somatropin.

Administration is possible not only as powder but also as atomized aqueous suspension. Administration can take place through the nose, bronchi or lung. For nasal administration it is particularly advantageous to choose an aqueous suspension because in this way irritation of the nasal mucous membranes and a stinging sensation due to organic solvents is avoided.

The active ingredient class of leukotriene antagonists is particularly suitable as area of use for the technology.

The preparations according to the invention can also be used for converting antisense active ingredients, that is to say oligonucleotides with a complementary base sequence to messenger RNA, into formulations which can be administered. The phosphorothioate oligonucleotides are preferred. It is moreover possible to use, besides local injection, also subcutaneous or intravenous administration as infusion or injection, and oral administration. However, dermal administration and inhalation are also conceivable.

The forms according to the invention can be employed in oral forms which can be used both from preparations in conventional tablets and in capsules. This area of application is opened up in particular by the possibility of also being able to produce suppository formulations, which is ensured by the stability of the nanoparticles according to the invention on stirring into the carrier matrices. It is advantageous in this connection that on rectal administration only a limited liquid volume is available, and the preparations according to the invention can be dispersed extremely well in the small liquid volume and be absorbed.

The advantageousness of the forms according to the invention can be generally stated in the following points:
greater relative bioavailability
smaller food effect
less variability.

Since it is also possible to use acrylates, lectins, caseinates, gelatins, chitosans, hyaluronic acids or mussel adhesion protein as shell polymers, it is also possible to produce mucoadhesive preparations with a nanoparticulate size.

The increased adhesiveness of nanoparticulate preparations may eventually also result in an increase in the bioavailability. This may be of interest in particular on nasal administration. An additional factor is that the adhesiveness of the nanoparticles to the nasal mucosa has a beneficial effect on the residence time, which otherwise tends to be too short, and may thus contribute to increasing the bioavailability.

The preparations according to the invention can also be employed on the eye. Especially in gel systems which react with an increase in viscosity at body temperature, the nanoparticulate systems according to the invention form a separate phase which is able to lead the active ingredient in nanoparticulate amorphous form to the eye and is homogeneously dispersed during the gel formation in the matrix.

It is likewise possible to produce contrast agents for medical diagnostic imaging such as X-ray methods, scintigraphy, ultrasound, magnetic resonance imaging, fluorescence angiography and opthalmology using the preparations according to the invention.

In cosmetics and dermatologicals it is possible to employ the core/shell nanoparticles according to the invention for protecting hydrolysis-sensitive active ingredients. In addition, preparations of this type are able, because of the small particle size, to facilitate penetration between the stratum corneum cells. In the cosmetics sector, the preparations according to the invention can be used in the formulation of perfumes and decorative cosmetics such as, for example, the incorporation of dyes or pigments into lipsticks, eyeliners, eyeshadows or nail varnishes. The preparations can also be employed in creams, gels and ointments.

A particular advantage of the nanoparticulate preparations according to the invention is that only a few ancillary substances are required. Apart from the polymeric coating matrix and the matrix polymers in the core, it is possible substantially to dispense with other surface-active ancillary substances.

Preparation Example 1

Preparation of a Ritonavir Dry Powder with an Active Ingredient Content in the Region of 20% by Weight a) Preparation of the Micronizate 3 g of ritonavir were stirred into a solution of 0.6 g of ascorbyl palmitate and 0.6 g of a copolymer of ethyl acrylate and methacrylic acid (1:1), (Kollicoat® MAE, BASF AG) in 36 g of isopropanol at 25° C., resulting in a cloudy suspension.

To convert the ritonavir and the Kollicoat into the form of a molecular dispersion, this coarse dispersion was mixed with 120 g of water at a mixing temperature of 200° C. for 0.3 s. To precipitate the ritonavir and the Kollicoat in colloidal form, this molecularly disperse solution was fed into another mixing chamber. There it was mixed with 490 g of an aqueous solution of 4.3 g of gelatin A 100 and 6.5 g of lactose in deionized water, which had been adjusted to pH=9.0 with 1 N NaOH, at 25° C. The pressure throughout the process was limited to 30 bar. After mixing, a colloidal ritonavir dispersion was obtained with a cloudy yellowish color.

Quasi-elastic light scattering was used to determine the average particle size as 260 nm with a variance of 42%. The average particle size increased by only 20 nm to 280 nm over the course of one hour. A colloidal ritonavir dispersion prepared analogously without Kollicoat shows an increase in the particle size by 400 nm over the course of one hour. These facts are summarized in Table 1.

TABLE 1

| Time after preparation of the colloidal dispersion | Colloidal dispersion with Kollicoat | Colloidal dispersion without Kollicoat |
|---|---|---|
| 3 min | 260 nm | 410 nm |
| 15 min | 259 nm | 485 nm |
| 30 min | 258 nm | 671 nm |
| 60 min | 281 nm | 835 nm | b) Drying of Dispersion a) to Give a Nanoparticulate Dry Powder

Spray drying of the product 1a) afforded a nanoparticulate dry powder. The active ingredient content in the powder was determined by chromatography to be 19.84% by weight. The dry powder dissolves in drinking water to form a cloudy yellowish dispersion (hydrosol) with an average particle size of 306 nm with a variance of 48%. The average particle size increased by only about 30 nm to 349 nm over the course of one hour. A colloidal ritonavir dispersion prepared analogously without Kollicoat shows an increase in the particle size by about 350 nm over the course of one hour. These facts are summarized in Table 2.

TABLE 2

| Time after preparation of the colloidal dispersion | Colloidal dispersion with Kollicoat | Colloidal dispersion without Kollicoat |
|---|---|---|
| 3 min | 306 nm | 585 nm |
| 15 min | 307 nm | 726 nm |
| 30 min | 324 nm | 815 nm |
| 60 min | 349 nm | 938 nm | c) Wide-Angle X-Ray Scattering

Figure 1:
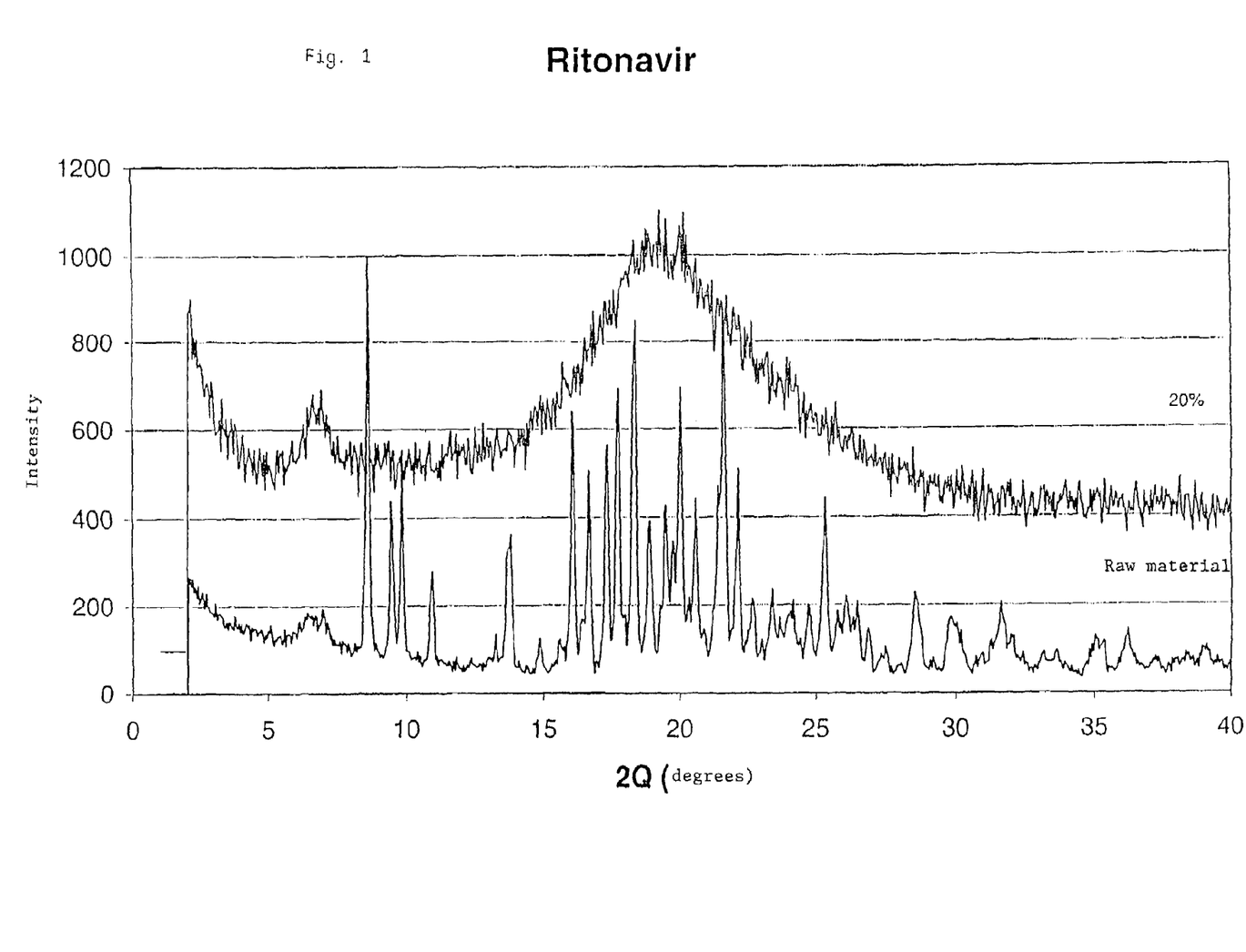
FIG. 1 depicts scattering plots for active ingredient and dry powder.

The scattering plots for active ingredient (top) and dry powder from 1b) (bottom) are depicted in FIG. 1. The ritonavir starting material is crystalline, as proven by the X-ray diagram which is characterized by a number of sharp interferences. In contrast thereto, the scattering plot for the dry powder shows only diffuse, broad interference maxima which are typical of an amorphous material. The active ingredient is accordingly in X-ray amorphous form in the dry powder prepared as in 1b). This also applies to the ancillary substances lactose and ascorbyl palmitate which are otherwise crystalline.

Preparation Example 2

Preparation of a Ciclosporin Dry Powder with an Active Ingredient Content in the Region of 20% by Weight a) Preparation of the Micronizate 3 g of ciclosporin were stirred into a solution of 0.6 g of ascorbyl palmitate and 0.6 g of Kollicoat® MAE (BASF AG) in 36 g of isopropanol at 25° C., resulting in a slightly cloudy suspension.

To convert the ciclosporin A and the Kollicoat into the form of a molecular dispersion, this coarse dispersion was mixed with 120 g of water at a mixing temperature of 200° C. for 0.3 s. To precipitate the ciclosporin and the Kollicoat in colloidal form, this molecularly disperse solution was fed into another mixing chamber. There it was mixed with 490 g of an aqueous solution of 4.3 g of gelatin A 100 and 6.5 g of lactose in deionized water, which had been adjusted to pH=9.0 with 1 N NaOH, at 25° C. The pressure throughout the process was limited to 30 bar. After mixing, a colloidal ciclosporin A dispersion was obtained with a cloudy white color.

Quasielastic light scattering was used to determine the average particle size as 249 nm with a variance of 42%. The average particle size did not increase within the accuracy of measurement over the course of one hour. A colloidal ciclosporin dispersion prepared analogously without kollicoat shows an increase in the particle size by 250 nm over the course of one hour. These facts are summarized in Table 3.

TABLE 3

| Time after preparation of the colloidal dispersion | Colloidal dispersion with Kollicoat | Colloidal dispersion without Kollicoat |
|---|---|---|
| 3 min | 249 nm | 330 nm |
| 15 min | 257 nm | 364 nm |
| 30 min | 251 nm | 410 nm |
| 60 min | 248 nm | 580 nm | b) Drying of Dispersion a) to Give a Nanoparticulate Dry Powder

Spray drying of the product 2a) afforded a nanoparticulate dry powder. The active ingredient content in the powder was determined by chromatography to be 20.03% by weight. The dry powder dissolves in drinking water to form a cloudy white dispersion (hydrosol) with an average particle size of 263 nm with a variance of 48%. The average particle size did not increase within the accuracy of measurement over the course of one hour. A colloidal ciclosporin dispersion prepared analogously without Kollicoat shows an increase in the particle size by about 150 nm over the course of one hour. These facts are summarized in Table 4.

TABLE 4

| Time after preparation of the colloidal dispersion | Colloidal dispersion with Kollicoat | Colloidal dispersion without Kollicoat |
|---|---|---|
| 3 min | 263 nm | 435 nm |
| 15 min | 259 nm | 463 nm |
| 30 min | 264 nm | 518 nm |
| 60 min | 267 nm | 575 nm |

Preparation Example 3

A micronizate containing propafenone as active ingredient was prepared in analogy to example 1.

Preparation Example 4

A micronizate which, in place of the polymer Kollicoat® MAE, contained as polymer a poly(D,L-lactide-co-glycolide) (49 mol % D,L-lactide, 51 mol % glycolide) was prepared in analogy to example 2.

Preparation Example 5

Preparation of a Canthaxanthin Dry Powder with an Active Ingredient Content in the Region of 5% a) Preparation of the Micronizate 15 g of canthaxanthin were stirred into a solution of 6 g of ethoxyquin and 45 g of Kollicoat MAE in 400 g of tetrahydrofuran at 25° C., resulting in a cloudy suspension.

To convert the canthaxanthin into the form of a molecular dispersion, this coarse dispersion was pumped at a flow rate of 1.8 kg/h through a heat exchanger and thereby heated to a temperature of 161.5° C. To precipitate the canthaxanthin and the Kollicoat in colloidal form, this molecularly disperse solution was fed, 1.4 seconds after reaching the temperature of 161.5° C., into another mixing chamber. There it was mixed with 9 600 g of an aqueous solution of 30 g of gelatin B 200 and 25 g of sucrose in deionized water, which had been adjusted to pH=11.8 with 1 N NaOH, at 25° C. The pressure throughout the process was limited to 60 bar. After mixing, a colloidal canthaxanthin dispersion was obtained with a cloudy reddish color.

Quasi-elastic light scattering was used to determine the average particle size as 796 nm with a variance of 81%.

b) Drying of Dispersion a) to Give a Nanoparticulate Dry Powder

Working up in a rotary evaporator and subsequent spray drying of the product 1a) afforded a nanoparticulate dry powder. The active ingredient content in the powder was determined by UV/VIS spectroscopy to be 5.75% by weight. The dry powder dissolves in water at pH values >7 to form a cloudy reddish dispersion (hydrosol) with an average particle size of 722 nm with a variance of 43%.

Preparation Example 6

Preparation of an Astaxanthin Dry Powder with an Active Ingredient Content in the Region of 25% by Weight a) Preparation of the Micronizate 1 g of astaxanthin was stirred into a solution of 3 g of a methacrylic acid/methyl methacrylate copolymer in the ratio 1:1 (Eudragit L 100, Röhm GmbH) in 200 g of tetrahydrofuran at 25° C. To convert the astaxanthin into the form of a molecular dispersion, this dispersion was pumped at a flow rate of 1.8 kg/h through a heat exchanger and thereby heated to a temperature of 73° C. To precipitate the astaxanthin and the Eudragit L 100 in colloidal form, this molecularly disperse solution was fed into another mixing chamber. There it was mixed with 10 000 g of deionized water at 25° C. The pressure throughout the process was limited to 30 bar. After the mixing, a colloidal astaxanthin dispersion was obtained with a reddish color.

Quasi-elastic light scattering was used to determine the average particle size as 256 nm with a variance of 56%.

b) Drying of Dispersion a) to Give a Nanoparticulate Dry Powder

Working up in a rotary evaporator and subsequent spray drying of the product 1a) afforded a nanoparticulate dry powder. The active ingredient content in the powder was determined by UV/VIS spectroscopy to be 24.3% by weight. The dry powder dissolves in alkaline water to form a red dispersion (hydrosol) with an average particle size of 273 nm with a variance of 53%.

Preparation Example 7

Preparation of an Astaxanthin Dry Powder with an Active Ingredient Content in the Region of 25% by Weight a) Preparation of the Micronizate 2 g of astaxanthin were stirred into a solution of 6 g of Eudragit L 100 (Röhm GmbH) in 200 g of tetrahydrofuran at 25° C. To convert the astaxanthin into the form of a molecular dispersion, this dispersion was pumped at a flow rate of 2.0 kg/h through a heat exchanger and thereby heated to a temperature of 73° C. To precipitate the astaxanthin and the Eudragit L 100 in colloidal form, this molecularly disperse solution was fed into another mixing chamber. There it was mixed with 10 000 g of deionized water at 25° C. The pressure throughout the process was limited to 30 bar. After mixing, a colloidal astaxanthin dispersion was obtained with a reddish color.

Quasi-elastic light scattering was used to determine the average particle size as 178 nm with a variance of 22%.

b) Drying of Dispersion a) to Give a Nanoparticulate Dry Powder

Working up in a rotary evaporator and subsequent spray drying of the product 1a) afforded a nanoparticulate dry powder. The active ingredient content in this powder was determined by UV/VIS spectroscopy to be 22.7% by weight. The dry powder dissolves in alkaline water to form a cloudy reddish dispersion (Hydrosol) with an average particle size of 175 nm with a variance of 25%.

The nanoparticles according to the invention can be used, for example, to produce the following dosage forms:

1. Tablet

10% by weight of the nanoparticulate preparation (on lactose as carrier) are mixed with 10% by weight of sucrose, 28% by weight of microcrystalline cellulose, 3% by weight of Kollidon Va. 64 and 0.2% by weight of Aerosil and then directly compressed. The tablet weight is 250 mg. The diameter is 8 mm. The hardness 150 N, the disintegration in water 13 min.

2. Patch

A patch with a reservoir of 17.5% by weight of polystyrene and 17.5% by weight of polyvinylacetate and 30% by weight of the nanoparticles according to the invention was produced.

3. Oil-in-Water Cream 24 g of liquid paraffin, 5 g of Cremophor S 9 (polyethylene glycol stearate), 6 g of beeswax, 2 g of Cutina CP (cetyl palmitate), 3 g of glycerol and 60 g of water form the basis of the cream into which 20 g of the nanoparticulate preparation according to the invention are stirred.

For fabrication, Cremophor is dissolved in the lipid phase and this mixture is mixed with water with vigorous stirring.

Stirring is continued until cold, and then the nanoparticulate preparation is added and homogenized.

4. Formulation for Topical Use

A preparation for topical use with the nanoparticulate core/shell preparations was obtained as follows: (in g/100 g)

0.14 g of methylparaben and 0.1 g of propylparaben plus 0.1 g of EDTA dihydrate are dissolved in 78.42 g of water at 80° C. After being allowed to cool to about 30° C., 20 g of the nanoparticles according to the invention are added as powder and homogenized by stirring. Subsequently 0.8 g of Carbomer 934 P and 0.44 g of NaOH are added.

5. Gel

Propylene glycol 20 g, poloxamer 188 5 g, poloxamer 407 22 g, NaCl 1 g, water 51 g, micronizate from example 1 20 g.

6. Eye Drops 10 g of micronizate from example 1, 14 g of Kollidon K 25, preservative as required, water ad 100 g.

7. Aerosol

Preparation of a powder formulation from:

a nanoparticulate formulation with 75 mg of budesonide, to an aqueous colloidal suspension of which 1400 g of lactose are added. The mixture is then spray-dried. The particle size of the resulting powder is 7 μm, the moisture content is 0.8% by weight.

Preparation with propellant:

0.25% by weight of a nanoparticulate budesonide preparation is introduced with a mixture of 4% by weight of ethanol and water (50:50) and 95.75% by weight of 1,1,1,2-tetrafluoroethane into an aluminum vessel under pressure.

8. Plaster

7% by weight of glycol are added to a mixture of 6% by weight of polyacrylic acid and 5% by weight of sodium polyacrylate plus 0.5% by weight of Aerosil 200. This mixture is homogenized by stirring. The mixture is then added to a solution of 0.03% by weight of EDTA in 65% by weight of water. To this is further added 0.3% by weight of polyoxyethylene sorbitan monostearate with heating to 50° C. Finally, the nanoparticulate powder according to the invention is stirred into the mixture, and the composition is applied to a nonwoven plaster base.

9. Injectable Depot Gel

10% by weight of the nanoparticles according to the invention, 30% by weight of a lactic acid/glycol copolymer, 10% by weight of ethanol, 50% by weight of isotonic saline 10. Effervescent Tablet 217 g of propafenone micronizate from preparation example 3

200 g of potassium bicarbonate 205.7 g of citric acid 142.1 g of instant sugar
  32.0 g of Macrogol 200
  2 g of lemon flavor
  1.2 g of saccharin The mixture was compressed under conventional conditions to a tablet with a thickness of 5.9 mm and a weight of 2.9 g.

Disintegration in water (beaker): 9 min.

We claim:

1. A process for preparing a nano-particulate preparation of a pharmaceutical or cosmetic active ingredient with a core/shell structure, in which an X-ray amorphous active ingredient is present in the core together with one or more copolymers of acrylates, methacrylates, methacrylic acid or acrylic acid, and the shell consists of a stabilizing coating matrix,
   the process comprising mixing an active ingredient/polymer solution or precipitate with an aqueous solution of a polymeric coating material continuously in a mixing chamber by spraying the two components as a compact jet into a mixing chamber,
   wherein said polymeric coating material is selected from the group consisting of gelatin, chitosan, alginates, casein, caseinates, and homopolymers of acrylic acid,
   wherein the particle size of the core/shell structure is in the range of 0.05 to 0.9 μm, and
   wherein the core of the preparation has at least two separate phases.

2. The process as claimed in claim 1, wherein one phase of the core consists of amorphous particles of the active ingredient, and the other phase comprises a molecular dispersion of the active ingredient in a polymer matrix.

3. The process as claimed in claim 1, wherein one phase of the core consists of amorphous active ingredient, and the other phase being comprises a polymer matrix free of active ingredient.

4. The process as claimed in claim 1, wherein the core polymers are suitable for pharmaceutical and cosmetic applications and are insoluble or only partly soluble in water.

5. A process for preparing a nano-particulate preparation of a pharmaceutical or cosmetic active ingredient with a core/shell structure, in which an X-ray amorphous active ingredient is present in the core together with one or more copolymers of acrylates, methacrylates, methacrylic acid or acrylic acid, and the shell consists of a stabilizing coating matrix,
   the process comprising mixing an active ingredient/polymer solution or precipitate with an aqueous solution of a polymeric coating material continuously in a mixing chamber by spraying the two components as a compact jet into a mixing chamber,
   wherein said polymeric coating material is selected from the group consisting of gelatin, chitosan, alginates, casein, caseinates, and homopolymers of acrylic acid,
   wherein the particle size of the core/shell structure is in the range of 0.05 to 0.9 and
   wherein the coating matrix of the nanoparticulate preparation comprises polymeric peptides.

6. A process for preparing a nano-particulate re pharmaceutical or cosmetic metic active ingredient with a core/shell structure, in which an X-ray amorphous active ingredient is present in the core together with one or more copolymers of acrylates, methacrylates, methacrylic acid or acrylic acid, and the shell consists of a stabilizing coating matrix,
   the process comprising mixing an active ingredient/polymer solution or precipitate with an aqueous solution of a polymeric coating material continuously in a mixing chamber by spraying the two components as a compact jet into a mixing chamber,
   wherein said polymeric coating material is selected from the group consisting of gelatin, chitosan, alginates, casein, caseinates, and homopolymers of acrylic acid,
   wherein the particle size of the core/shell structure is in the range of 0.05 to 0.9 μm, and
   wherein the preparation comprises gelatin as coating polymer.

7. A process for preparing a nano-particulate preparation of a pharmaceutical or cosmetic active ingredient with a core/shell structure, in which an X-ray amorphous active ingredient is present in the core together with one or more copolymers of acrylates, methacrylates, methacrylic acid or acrylic acid, and the shell consists of a stabilizing coating matrix, the process comprising mixing an active ingredient/polymer solution or precipitate with an aqueous solution of a polymeric coating material continuously in a mixing chamber by spraying the two components as a compact jet into a mixing chamber, wherein said polymeric coating material is selected from the group consisting of gelatin, chitosan, alginates, casein, caseinates, and homopolymers of acrylic acid, wherein the particle size of the core/shell structure is in the range of 0.05 to 0.9 µm, and wherein the preparation comprises casein or sodium caseinate as coating matrix.

8. The process as claimed in claim 1, wherein the process produces a hydrosol of the said nanoparticulate preparation.

9. The process as claimed in claim 8, in which wherein the sizes of the hydrosol nanoparticles increase by less than 50% in the first hour after preparation of the hydrosol.

10. The process for producing preparations as claimed in claim 1, further comprising preparing a solution of the active ingredient in an organic solvent which is at least 10% by weight miscible in water, mixing this solution with the core polymer or a solution of the core polymer in an organic solvent, and bringing the resulting mixture into contact with an aqueous solution of the coating polymer.

11. A nanoparticulate preparation of a pharmaceutical or cosmetic active ingredient with a core/shell structure wherein an X-ray amorphous active ingredient is present in the core together with one or more polymers selected from the group consisting of copolymers of acrylates, methacrylates, methacrylic acid and acrylic acid, wherein the shell consists of a stabilizing coating matrix, wherein said polymeric coating material is selected from the group consisting of gelatin, chitosan, alginates, casein, caseinates, and homopolymers of acrylic acid, wherein the particle size of the core/shell structure being in the range of 0.05 to 0.9 µm, wherein the core of the preparation has at least two separate phases, and wherein the nanoparticulate preparation is obtained by mixing an active ingredient/core polymer solution or precipitate with the an aqueous solution of the polymeric coating material continuously in a mixing chamber.

12. The preparation of claim 11, wherein on redissolving, the preparation has the same particle size distribution, with a variation of 20%, as the initial preparation.

* * * * *